United States Patent

Nishiura et al.

Patent Number: 5,690,957
Date of Patent: Nov. 25, 1997

[54] PROSTAGLANDIN DERIVATIVES

[75] Inventors: Akio Nishiura; Takuya Seko; Ryoji Matsumoto; Shin-ichi Hamano, all of Osaka, Japan

[73] Assignee: Ono Pharmaceutical Co., Ltd., Osaka, Japan

[21] Appl. No.: 699,700

[22] Filed: Aug. 14, 1996

[30] Foreign Application Priority Data

Aug. 16, 1995 [JP] Japan ..................... 7-230763

[51] Int. Cl.$^6$ ................. C07C 405/00; A61K 31/557
[52] U.S. Cl. ................. 424/450; 424/488; 536/103; 554/228; 560/121
[58] Field of Search .............. 560/121; 554/228; 424/450, 488; 536/103

[56] References Cited

FOREIGN PATENT DOCUMENTS 59-206349  11/1984  Japan .

Primary Examiner—Robert Gerstl
Attorney, Agent, or Firm—Watson Cole Stevens Davis, PLLC

[57] ABSTRACT

Prostaglandin E, ester derivatives of the formula (I):

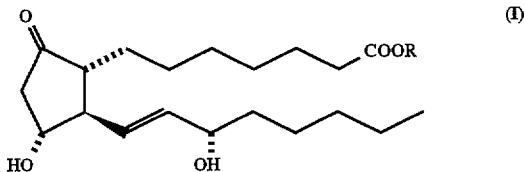

wherein R is (i) $-CH_2CH_2-O-CO-R^1$ (ii) $-CH_2CH_2-O-CO-CH_2-O-R^2$, and $R^1$ and $R^2$ each independently is C10–20 alkyl;

and cyclodextrin clathrates thereof, liposome formulations containing them, and pharmaceutical compositions containing them as active ingredient.

The compounds of formula (I) have the effect of increasing blood flow and are useful for the prevention and/or treatment of peripheral circulatory disorder, decubitus, or skin ulcers, or for the maintenance of blood flow.

12 Claims, No Drawings

PROSTAGLANDIN DERIVATIVES

BACKGROUND OF THE INVENTION

The present invention relates to prostaglandin $E_1$ (hereinafter abbreviated as $PGE_1$) ester derivatives or cyclodextrin clathrates thereof, liposome formulations containing them, and pharmaceutical compositions containing them as active ingredient.

$PGE_1$ is represented by the following structural formula:

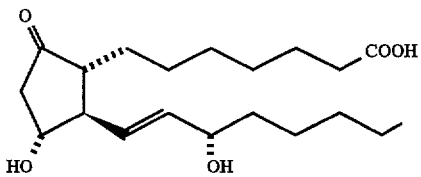

and has various physiological properties. In particular, $PGE_1$ has a hypotensive, vasodilatory, blood flow increasing and anti-platelet effect on blood vessels.

Because of its various physiological properties, $PGE_1$ has been applied in medicine. Already, $PGE_1$ has been used for treatment of peripheral arterial occlusive disease, thrombotic anginetic obliterence, etc., and for maintenance of blood flow after reconstructive vascular surgery, maintenance of low blood pressure levels during a surgical operation, as an anesthetic, etc.

Peripheral circulatory disorder is a disease accompanied by various ischemic symptoms such as pain, psychroesthesia, etc., in which obstructions are induced by thrombus formation in peripheral blood vessels, and following ulcer formation. In order to treat this disorder, it is necessary to improve the blood circulation by increasing blood flow in the peripheral circulation.

Because $PGE_1$ increases blood flow, it could be useful for treating peripheral circulatory disease. However, the usefulness of $PGE_1$ in this regard is limited by the following phenomena:

(1) $PGE_1$ has many physiological properties. Therefore, if one physiological action of $PGE_1$ is applied to the therapy, other physiological effects of $PGE_1$ become side effects.

(2) $PGE_1$ is rapidly inactivated by its metabolizing enzyme in vivo.

Thus, if a large amount of $PGE_1$ is injected into the blood vessel at once, it acts not only on the peripheral circulation but also on the aortic series; therefore, there is a fear of causing serious hypotension. In order to prevent this problem, $PGE_1$ should be injected in controlled doses so that it acts on the peripheral circulation, but acts to a lesser degree on the aortic series.

On the other hand, it is known that $PGE_1$ is very rapidly metabolized. Accordingly, in order to maintain its blood flow increasing effect, it is required that $PGE_1$ be sequentially administered in vivo.

As a result of considering these phenomena in combination, it is desired to prepare a compound that is converted into $PGE_1$ in vivo after its administration. Furthermore, the rate of conversion should be moderately slow, so that the effect can be maintained.

It is described in the specification of Japanese Patent Kokai No. 59-206349, herein incorporated by reference, that compounds of the formula (A):

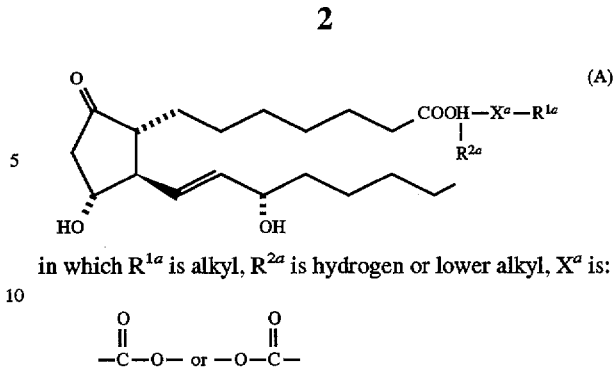

in which $R^{1a}$ is alkyl, $R^{2a}$ is hydrogen or lower alkyl, $X^a$ is:

$$-\overset{O}{\underset{\|}{C}}-O- \quad \text{or} \quad -O-\overset{O}{\underset{\|}{C}}-$$

have a hypotensive effect, anti-platelet effect etc., and are used as hypotensive agents and agents for treatment of thrombosis, and particularly, a compound which is converted into a fat emulsion is preferred.

The present inventors have searched for a compound that is gradually converted into $PGE_1$ in vivo after administering. As a result, the present inventors have found that this result may be achieved with compounds in which the carboxylic acid group at the 1-position of $PGE_1$ is esterified by a specific alcohol.

Further, the present inventors have also found that the effect may be improved by enclosing the compounds of the present invention in a closed vesicle comprising a phospholipid bilayer called a liposome.

SUMMARY OF THE INVENTION

The present invention accordingly provides prostaglandin $E_1$ ester derivatives of formula (I):

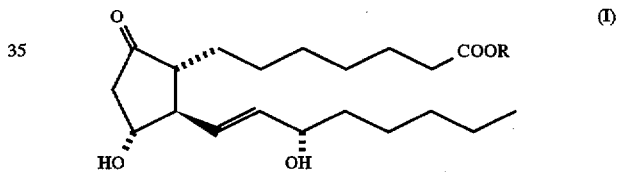

wherein R is (i) —$CH_2CH_2$—O—CO—$R^1$, or (II) —$CH_2CH_2$—O—CO—$CH_2$—O—$R^2$, and $R^1$ and $R^2$ each independently is C10–20 alkyl; or a cyclodextrin clathrate thereof. Compounds of formula (I) have excellent selectivity and maintenance of action.

The present invention also provides liposome formulations comprising a compound of formula (I) or a cyclodextrin clathrate thereof as an active ingredient. Such liposome formulations display excellent maintenance of activity and release of the active ingredient.

The invention also includes pharmaceutical compositions comprising a compound of formula (I) or a cyclodextrin clathrate thereof as an active ingredient.

$PGE_1$ derivatives of formula (I) are different from those of formula (A) in the following ways. First, in formula (A) compounds, a methylene chain (—$CH_2$—) or methylene chain substituted by an alkyl group:

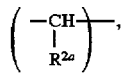

exists in between the carboxyl group of $PGE_1$ and ester bond represented by $X^a$ (—COO— or —OCO—). However, in the corresponding moiety of the present invention when R is represented by (i) —$CH_2$—$CH_2$—O—CO—$R^1$, it is bonded to the carboxyl group at $PGE_1$ via an ethylene chain (—$CH_2CH_2$—), or when R is represented by (ii) —$CH_2CH_2$—O—CO—$CH_2$—O—$R^2$, it is bonded to $PGE_1$ via ethylene, and furthermore, it is bonded to $R^2$ via an ether bond (—$CH_2$—O—).

In addition, there is a functional difference in that liposome formulations of compounds of the present invention have better selectivity for the peripheral circulation and maintenance of action when compared with known compounds.

DETAILED DESCRIPTION OF THE INVENTION

Throughout the specification, it will be understood by those skilled in the art that all isomers are included in the present invention. For example, the term "alkyl group" includes straight-chain groups and branched-chain groups.

In the formula (I), a C10–20 alkyl group represented by $R^1$ or $R^2$ is decyl, undecyl, dodecyl, tridecyl, tetradecyl, pentadecyl, hexadecyl, heptadecyl, octadecyl, nonadecyl, eicosyl or an isomer thereof.

Preferably, $R^1$ is C10–12 alkyl or an isomer thereof, and $R^2$ is C11–17 alkyl or an isomer thereof. More preferably, $R^1$ is undecyl and $R^2$ is dodecyl or hexadecyl.

Cyclodextrin clathrates of the $PGE_1$ derivatives of the formula (I) may be prepared by the method described in the specification of U.S. Pat. Nos. 3,816,393 or 4,054,736, both of which are herein incorporated by reference, using (α-, β- or γ-cyclodextrins or a mixture thereof.

Converting $PGE_1$ derivatives of formula (I) into their cyclodextrin clathrates serves to increase their stability and solubility in water and is therefore beneficial because it facilitates administration of the invention compounds as pharmaceuticals.

Compounds of formula (I) may be prepared by elimination of the $R^3$ group of a compound of formula (II)

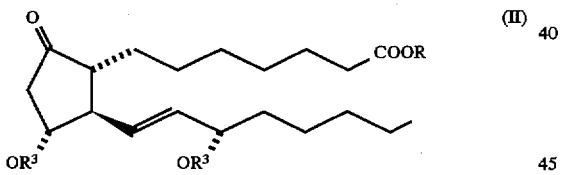
(II)

wherein R is as defined for formula (I) and $R^3$ is a hydroxyl-protecting group which may be eliminated under acidic conditions, for example, with tetrahydropyran-2-yl, methoxymethyl or 2-ethoxyethyl. The elimination reaction of the $R^3$ group may be carried out in an aqueous solution of organic acid (e.g., acetic acid or p-toluenesulfonic acid) or inorganic acid (e.g., hydrochloric acid or sulfuric acid), in the presence of a water-miscible organic solvent (e.g., a lower alkanol (such as methanol or ethanol) or an ether (such as dioxane or tetrahydrofuran) at a temperature between room temperature and 75° C. The above-mentioned reaction is preferably carried out in a mixed solvent comprising acetic acid, water and tetrahydrofuran at a temperature of 40° C. to 50° C.

The compounds of formula (II) may be prepared by reacting a free carboxylic acid corresponding to a compound of formula (II) with a compound of formula (III):

HO—$CH_2CH_2$—O—CO—$R^1$ (III);

or a compound of formula (IV)

HO—$CH_2CH_2$—O—CO—$CH_2$—O—$R^2$ (IV), wherein $R^1$ and $R^2$ are as hereinbefore defined, said reaction being carried out in an inert organic solvent (e.g., an ether (such as tetrahydrofuran or dioxane)) in the presence of triphenylphosphine or diethylazodicarboxylate (DEAD) at a temperature of 0° C. to room temperature.

One of the free carboxylic acids used to prepare compounds of formula (II) is (13E)-(11α, 15S)-9-oxo-11, 15-bis (tetrahydropyran-2-yloxy)prost-13-enoic acid, which is a known compound described in J. Am. Chem Soc., 92, 2586 (1970), herein incorporated by reference.

The other free carboxylic acids used to prepare compounds of formula (II), and the compounds of formulae (III) and (IV), are known per se, or may be easily prepared from known compounds by methods known per se.

For example, the compounds of formulae (III) and (IV) may be prepared by the method described in the following Scheme (A) and Scheme (B), respectively.

Scheme A

ClCOR¹ $\xrightarrow[\text{Py, acetone}]{\text{HOCH}_2\text{CH}_2\text{OH}}$ HOCH₂CH₂OCOR¹

(III)

Scheme B

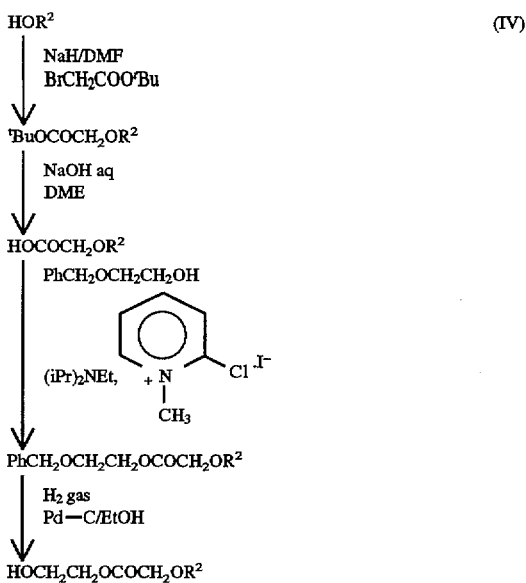

In the above-mentioned Schemes, $R^1$ and $R^2$ are as hereinbefore defined and the abbreviations have the following meanings.

Py: pyridine,
DMF: dimethylformamide,
$^t$Bu: tert-butyl,
DME: dimethoxyethane,
iPr: isopropyl,
Et: ethyl,
THF: tetrahydrofuran,
Ph: phenyl,
EtOH: ethanol.

In spite of having a potent and maintainable blood flow increasing effect, $PGE_1$ ester derivatives of the formula (1), and cyclodextrin clathrates thereof, have only a weak hypotensive effect, and therefore, may be used as agents for the prevention and/or treatment of peripheral circulatory disorder (e.g., peripheral arterial occlusive disease or thrombotic anginetic obliterence), decubitus, skin ulcers (e.g., ulcers resulting from burns, diabetic ulcers, stenosis of femoral artery and operation stress), and for the maintenance of blood flow after reconstructive vascular surgery.

The blood flow increasing effect and hypotensive effect of the compounds of the present invention were determined by the following experiment.

EXAMPLES

Male rats weighing 200–350 g were anesthetized with urethane (25% urethane, 6 ml/kg, s.c.). The carotid artery and jugular vein were cannulated with polyethylene tubes for measurement of blood pressure and for drug injection, respectively. Blood pressure was obtained with a disposable pressure transducer kit (Spectramed, Ltd) and recorded with a recticoder (model RJG-4128, Nihon kohden, Ltd). Blood flow was monitored as cutaneous blood flow of the dorsum pedis using an attachment-type laser-Doppler flowmeter (model ALF21, Advance, Ltd). Measurements were taken until the values recovered to the level observed before injection of drugs. Injection time was about 10 seconds. The hypotensive effect and blood flow increasing effect were calculated as the maximal hypotensive activity (mmHg) and the area under the curve (AUC) after injection of drugs, respectively.

The results were represented by the dose required to obtain an effective increase in blood flow (main effect), and by the hypotensive effect (side effect) at the same dose.

The compounds of the present invention were administered in the form of a liposome formulation (as prepared in Example 4 below). As a comparative compound, $PGE_1$ 1-decanoyloxyethyl ester (described in Example 10 of the specification of Japanese Patent Kokai No. 59-206349) was administered in the form of a lipid emulsion (prepared in Reference Example 8 in the present specification).

The effectiveness of increasing blood flow was determined by the following method. It is known that a $PGE_1$ lipid emulsion (commercially available) shows efficacy at 5 µg/kg i.v. injection in the rat disease model [described in Drug Exp. Clin. Res., 12, 917 (1986), herein incorporated by reference]. In the above-described experimental assessment system for the compounds of the present invention, the AUG for this $PGE_1$ lipid emulsion (5 µg/kg, i.v.) was 771 on the blood flow increasing effect; thus this value was chosen as an effective value for increase in blood flow.

The results of this experiment are shown in Table 1, below.

TABLE 1

| Example | Dose (µg/kg) | Total AUC | Blood flow increasing effect — Dose (A) required to obtain AUC = 771 (µg/kg) | Hypotensive effect — Maximum hypotension (mmHg) | Hypotensive effect — Maximum hypotension on dose (A) (mmHG) |
|---|---|---|---|---|---|
| 1 | 1 | 175 |  | 3 |  |
|  | 3 | 1914 | 1.47 | 7 | 4.3 |
|  | 10 | 3528 |  | 13 |  |
| 2 | 3 | 329 |  | 3 |  |
|  | 10 | 807 | 8.14 | 7 | 6.1 |
|  | 30 | 3248 |  | 20 |  |
| 3 | 1 | 227 |  | 2 |  |
|  | 3 | 4028 | 1.14 | 9 | 2.8 |
|  | 10 | 5391 |  | 9 |  |
| Comparative compound | 1 | 92 |  | 1 |  |
|  | 3 | 222 | 16.70 | 9 | 30.2 |
|  | 10 | 498 |  | 18 |  |

Table 1 shows the following facts:
(1) Blood flow increasing effect (main effect) of the compounds of the present invention is about 2 to 15 times better than that of the comparative compound.
(2) On the other hand, hypotensive effect (side effect) of the compounds of the present invention at the effective dose is one-tenth to one-fifth that of the comparative compound.

Therefore, the compounds of the present invention are significantly better than the comparative compound, for the prevention and/or treatment of peripheral circulatory disorder, decubitus, skin ulcers, or for maintenance of blood flow after reconstructive vascular surgery.

The toxicity of the compounds of the present invention is very low and therefore the compounds of the present invention may be suitable for pharmaceutical use.

For the above described purposes, compounds of the formula (I), and cyclodextrin clathrates of them, may be normally administered systemically or partially, usually by parenteral administration.

The doses to be administered are determined depending upon, for example, age, body weight, symptom, the desired therapeutic effect, the route of administration, and the duration of treatment. In the human adult, the doses per person are generally from 0.1 µg to 500 µg, by parenteral administration (preferably intravenous administration), up to several times per day, or continuous administration from 1 to 24 hrs. per day intravenously.

As mentioned above, the doses to be used depend upon various conditions. Therefore, there are cases in which doses lower than or greater than the ranges specified above may be used.

The compounds of the present invention may be administered in the form of, for example, injections, liniments or suppositories for parenteral administration.

Injection formulations for parenteral administration include sterile aqueous or non-aqueous solutions, suspensions and emulsions. Aqueous solutions and suspensions may include distilled water for injection or physiological salt solution. Non-aqueous solutions and suspensions may, for example, include propylene glycol, polyethylene glycol, vegetable oil such as olive oil, alcohol such as ethanol or POLYSORBATE80®.

Injection formulations may comprise additional ingredients other than inert diluents; e.g., preserving agents, wetting agents, emulsifying agents, dispersing agents, stabilizing agents, and assisting agents, e.g., agents to assist dissolution (e.g., glutamic acid or aspartic acid).

These formulations may be sterilized, for example, by filtration through a bacteria-retaining filter, by incorporation of sterilizing agents in the compositions, or by irradiation. They may also be manufactured in the form of sterile solid compositions which may be dissolved in sterile water or some other sterile diluent(s) for injection immediately before use.

Other compositions for parenteral administration include liquids for external use, and endermic liniments, ointment, suppositories for rectal administration and pessaries for vaginal administration which comprise one or more of the active compound(s) and may be prepared by methods known per se.

Furthermore, the present invention includes liposome formulations containing $PGE_1$ ester derivatives of the formula (I) or cyclodextrin clathrates thereof, as active ingredient.

The liposomes used in these formulations are uni- or multilammelar fine spherical vesicles comprising phosphatidylcholine (e.g., natural phospholipids derived from egg yolk or soya bean, and synthetic phospholipids such as dimyristoylphosphatidylcholine, distearoylphosphatidylcholine and dipalmitoylphosphatidylcholine) as the liposome membrane material. The encapsulation of the drugs into the liposomes enables delivery of the drugs to the targeted organ, and prolonged release of the drugs.

Additives other than the active ingredient, which are, for example, sugars (e.g., lactose or mannitol), neutral phospholipids (e.g., cholesterol or triglyceride) or charged lipids (e.g., phosphatidic acid or stearylamine) can be mixed into the liposome formulations.

The liposome formulations may be prepared by methods known per se. For example, suitable methods are described in detail in Liposome Technology Vol. 1, 2 and 3, edited by Gregoriadis, G. (published in 1993), herein incorporated by reference. $PGE_1$ ester derivatives of the formula (I), or cyclodextrin clathrates thereof, and liposome membrane material are in the ratio of from 1:1 to 1:400. The preferred ratio is from 1:10 to 1:200. The particularly preferred ratio is from 1:10 to 1:50.

The following Reference Examples and Examples illustrate, but do not limit, the present invention.

The solvents in the parentheses show the developing or eluting solvents and the ratios of the solvents used are by volume in chromatographic separations.

The solvents in the parentheses in NMR show the solvents used for measurement.

Reference Example 1

Lauric acid 2-hydroxyethyl ester

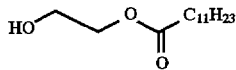

Under cooling with ice, ethylene glycol (434 mg) was dissolved into acetone (20 ml), and pyridine (632 mg) was added thereto and then lauroyl chloride (1532 mg) was added dropwise thereto. The temperature of the solution was warmed to room temperature, and it was stirred for 2 hours. The mixture was evaporated. To the residue was added water, and the solution was extracted with ethyl acetate. The organic layer was washed with water (three times), dried over magnesium sulfate and evaporated. The residue was purified by silica gel column chromatography (n-hexane:ethyl acetate=4:1) to give the title compound (1.63 g) having the following physical data.

TLC:Rf:0.38 (n-hexane:ethyl acetate=4:1).

Reference Example 2

(13E)-(11α, 15S)-9-oxo-11, 15-bis (tetrahydropyran-2-yloxy)prost-13-enoic acid 2-(dodecanoyloxy)ethyl ester

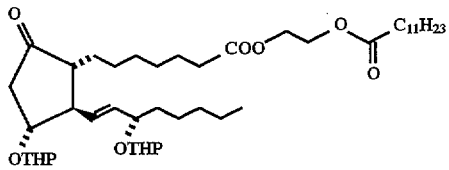

Under cooling with ice, (13E)-(11α, 15S)-9-oxo-11, 15-bis (tetrahydropyran-2-yloxy)prost-13-enoic acid (365.4 mg) was dissolved into tetrahydrofuran (THF) (5 ml), and triphenylphosphine (366.5 mg) and the alcohol derivative prepared in Reference Example 1 (341.6 mg) added thereto. After a solution of diethylazodicarboxylate (DEAD) (243.6 mg) in THF (1 ml) was added dropwise to the reaction solution, the temperature of the reaction solution was warmed to room temperature and it was stirred for 1.5 hours. To the reaction solution was added water and the solution was extracted with ethyl acetate (twice). The organic layer was washed with a saturated aqueous solution of sodium chloride, dried over magnesium sulfate and evaporated. The residue was purified by silica gel column chromatography (n-hexane:ethyl acetate=4:1) to give the title compound (466 mg) having the following physical data.

TLC: Rf 0.42 (n-hexane:ethyl acetate=4:1).

Reference Example 3

Hexadecyloxyacetic acid t-butyl ester

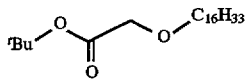

Sodium hydride (532.5 mg) was suspended in DMF (15 ml) and a solution of hexadecanol (4.0 g) in DMF (10 ml) was added dropwise thereto and sodium iodide (15 mg) was added thereto. After stirring for one hour at 80° C., a highly viscid milky solution was obtained. The temperature of the solution was cooled to room temperature and α-bromoacetic acid t-butyl ester (2.6 g) was added thereto. After the reaction solution was stirred for one hour, water was added thereto for stopping the reaction. The mixture was extracted with a solvent mixture (n-hexane:ethyl acetate=1:1) (three times). The organic layer was washed with a saturated aqueous solution of sodium chloride, dried over magnesium sulfate and evaporated. The residue was purified by silica gel column chromatography (n-hexane:ethyl acetate=20:1) to give a mixture (2.53 g) of the title compound and hexadecyloxyacetic acid hexadecyl ester (by product).

TLC:Rf 0.45 (n-hexane:ethyl acetate=10:1),

NMR (CDCl$_3$): δ4.12 (t, J=5.8Hz), 4.06 (s), 3.52 (t, J=4.8Hz), 1.62 (m), 1.26 (m), 0.88 (t, J=7.0Hz).

Reference Example 4

Hexadecyloxyacetic acid

HOOCCH$_2$O—C$_{16}$H$_{33}$

The mixture of t-butyl ester derivative and hexadecyl ester derivative (prepared in Reference Example 3 (1.45 g)) was dissolved into dimethoxyethane (5 ml), 1N aqueous solution of sodium hydroxide (2 ml) was added thereto, and it was refluxed. This mixture was extracted with ether for removing impurity. The aqueous layer was acidified by adding 1N hydrochloric acid, and it was extracted with a solvent mixture (n-hexane:ethyl acetate=1:1) (three times), and washed with a saturated aqueous solution of sodium chloride, dried over magnesium sulfate and evaporated. The residue was purified by silica gel column chromatography (n-hexane:ethyl acetate=1:1) to give the title compound (698 mg) having the following physical data.

TLC: Rf 0.25 (n-hexane:ethyl acetate=1:1),

NMR: (CDCl$_3$): δ 4.10 (2H, s), 3.5 (2H, t, J=6.2Hz), 1.75–1.50 (2H, m), 1.36 (26H, m), 0.85 (3H, t, J=6.8Hz).

Reference Example 5

Hexadecyloxyacetic acid 2-(benzyloxy)ethyl ester

To a solution of the carboxyl acid derivative prepared in Reference Example 4 (698 mg) and 2-(benzyloxy)ethanol (710 mg) in dichloromethane (10 ml) was added diisopropylethylamine (2.2 ml), and 2-chloro-1-methylpyridinium iodide (891 mg), successively, and the reaction solution was stirred for 1.5 hours. Water was added to the reaction solution and the solution was extracted with dichloromethane (twice). The organic layer was washed with dilute hydrochloric acid and a saturated aqueous solution of sodium chloride, successively, dried over magnesium sulfate and evaporated. The residue was purified by silica gel column chromatography (n-hexane:ethyl acetate 10:1) to give the title compound (425 mg) having the following physical data. TLC: Rf 0.63 (n-hexane:ethyl acetate=3:1), NMR (CDCl$_3$): δ 7.30 (5H, m), 4.57 (2H, s), 4.34 (2H, t, J=4.8Hz), 4.10 (2H, s), 3.70 (2H, t, J=4.8Hz), 3.52 (2H, t, J=6.6Hz), 1.57 (4H, m), 1.27 (24H, m), 0.88 (3H, t, J=6.8Hz),

Reference Example 6

Hexadecyloxyacetic acid 2-hydroxyethyl ester

After 10% palladium-carbon (110 mg) was suspended in ethyl acetate, hydrogen gas was charged into the suspension. A solution of the benzyl derivative prepared in Reference Example 5 (365 mg) in ethyl acetate (5 ml) was added to the reaction solution and it was stirred for one hour under an atmosphere of hydrogen gas. After confirming the disappearance of the spot of starting material on TLC, the hydrogen gas was removed and the palladium-carbon was removed by using Celite®. The solvent was evaporated. The residue was purified by silica gel column chromatography (n-hexane:ethyl acetate=2:1) to give the title compound (275 mg) having the following physical data.

TLC: Rf 0.32 (n-hexane:ethyl acetate=2:1),

NMR (CDCl$_3$): δ 4.30 (2H, d, J=4.8Hz), 4.12 (2H, s), 3.85 (2H, m), 3.52 (2H, t, J=6.2Hz), 1.70–1.50 (2H, m), 1.26 (26H, m), 0.86 (3H, t, J=6.8Hz).

Reference Example 7

(13E)-(11α, 15S)-9-oxo-11, 15-bis (tetrahydropyran-2-yl)prost-13-enoic acid 2-(hexadecyloxyacetoxy)ethyl ester By the same procedure as in Reference Example 2, using the alcohol derivative (258 mg) prepared in Reference Example 6 instead of lauric acid 2-hydroxyethyl ester, the title compound (268 mg) having the following physical data was obtained.

TLC: Rf 0.45 (n-hexane:ethyl acetate=5:2).

Example 1

PGE$_1$ (dodecanoyloxy)ethyl ester

To a solution of bis (tetrahydropyran-2-yloxy) derivative (prepared in Reference Example 2 (460 mg)) in THF (2 ml) was added 65% acetic acid (20 ml) and the reaction solution was stirred for one hour at 45° C. The temperature of the reaction solution was cooled to room temperature and water was added to the reaction solution and the solution was extracted with ethyl acetate (three times). The organic layer was washed with water, a saturated aqueous solution of sodium bicarbonate and a saturated aqueous solution of sodium chloride, successively, dried over magnesium sulfate and evaporated. The residue was purified by silica gel column chromatography (n-hexane:ethyl acetate=1:1) to give the title compound (178 mg) having the following physical data.

TLC: Rf 0.60 (ethyl acetate),

NMR (CDCl$_3$): δ 5.77–5.48 (2H, m), 4.26 (4H, s), 4.20–3.97 (2H, m), 3.10–2.90 (1H, m), 2.83–2.67 (1H, m), 2.45–2.13 (7H, m), 2.07–1.93 (1H, m), 0.95–0.83 (6H, m).

Example 2

PGE$_1$ 2-(hexadecyloxyacetoxy)ethyl ester

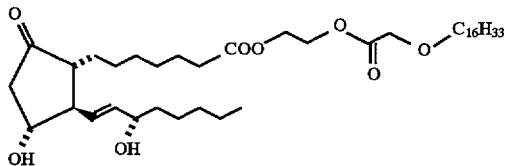

By the same procedure as in Example 1, using the bis(tetrahydropyran-2-yloxy) derivative (260 mg) prepared in Reference Example 7 instead of the bis(tetrahydropyran-2-yloxy) derivative used in Example 1, the title compound (145.5 mg) having the following physical data was obtained.
TLC: Rf 0.45 (n-hexane:ethyl acetate=1:3);

NMR (CDCl$_3$): δ 5.78–5.50 (2H, m), 4.24–4.20 (4H, m), 4.20–3.98 4H, m), 3.55 (2H, t, J=7.0Hz), 3.08–2.95 (1H, bs), 2.72 (1H, dd, J=12, 7.5Hz), 2.42–2.15 (5H, m), 2.15–1.90 (2H, m), 1.90–1.48 (10H, m), 1.48–1.18 (34H, m), 1.00–0.90 (6H, m).

Example 3

PGE$_1$ 2-(dodecyloxyacetoxy)ethyl ester

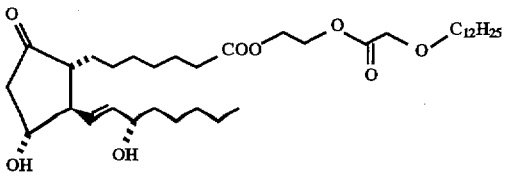

By the same procedures as in Reference Example 3, Reference Example 4, Reference Example 5, Reference Example 6, Reference Example 7 and Example 2, starting from tetradecanol instead of hexadecanol, the title compound having the following physical data was obtained.

NMR (CDCl$_3$): δ 5.78–5.48 (2H, m), 4.24–4.20 (4H, m), 4.20–3.98 (4H, m), 3.55 (2H, t, J=7.0Hz), 3.40–3.10 (1H, bs), 2.72 (1H, dd, J=12, 7.5Hz), 2.52–2.10 (5H, m), 2.15–1.90 (1H, m), 1.90–1.48 (8H, m), 1,48–1.18 (28H, m), 1.00–0.90 (6H, m).

Example 4

Preparation of the Liposome Formulations

Dimyristoylphosphatidylcholine (DMPC) (6 mg) and various PGE$_1$ ester derivatives of the present invention (3–90 μg) were dissolved in chloroform and a dry lipid film of the mixture was produced by freeze-drying, i.e., removing the chloroform and standing the mixture under reduced pressure for one hour.

The dry lipid film was dispersed into a 10% maltose solution (3 ml) by using a vortex mixer (type S-100, Taiyokagaku Inc.) and an aqueous suspension with a drug concentration 1, 3, 10, or 30 μg/ml was obtained. Small unilamellar liposomes were prepared from the above multilamellar liposome solutions by the following methods.

(1) Sonication Method

The multilamellar liposome solutions (3 ml) prepared by the above method were transferred into plastic tubes and were sonicated with a probe sonicator (type: SONIFIER cell disruptor 200, Branson) at the condition of 50% pulsed operation for 15 minutes. The sonicated solutions were passed through a membrane filter with a pore diameter of 0.2 μm to remove titanium particles and liposome formulations with a mean diameter of 40–70 nm were formed.

(2) Extrusion Method

In the extrusion apparatus (THE EXTRUDER, Lipex-Biomembranes Inc.), two polycarbonate membrane filters with pore diameter of 0.1 μm were stacked and the multilamellar liposome solutions (3 ml) prepared by the above method were added. The extrusion apparatus was put in the water bath maintained at 40°–50° C. After the multilamellar liposome solutions were passed through two stacked membrane filters three times, the obtained small unilamellar liposomes were passed through polycarbonate membrane filters with a pore diameter of 0.05 μm exchanged from 0.1 μm, three times. The mean diameter of the finally obtained liposome formulations were 50–60 μm.

Example 5

Preparation of the Liposome Formulations

By the same procedure as Example 4, using egg lecithin (6 mg) instead of dimyristoylphosphatidylcholine, and PGE$_1$ ester derivatives of the present invention (30 μg–600 μg), liposome formulations were formed.

Formulation Example 1

The liposome formulation of PGE$_1$ decanoyloxyethyl ester (prepared in Example 4) were divided into 1 ml vials and lyophilized to generate injection products.

Reference Example 8

Lipid Emulsion of PGE$_1$ 1-decanoyloxyethyl ester

Purified egg yolk phospholipid (48 mg), PGE$_1$ 1-decanoyloxyethyl ester (15 μg–450 μg), sodium oleate (1 mg) and phosphatidic acid (1 mg) were added to purified soybean oil (200 mg) and dissolved at 40°–70° C. Distilled water (2 ml) was added and the mixtures were emulsified crudely for 30 minutes using a high-speed homogenizer. Furthermore, to the obtained emulsions were added glycerin (10 mg) and distilled water for injection (800 μl, 20°–40° C.), successively. They were emulsified for 30 minutes using a probe sonicator and homogeneous fine lipid emulsions (mean diameter: 200–400 nm) were formed.

We claim:

1. A prostaglandin E$_1$ ester derivative of formula (1):

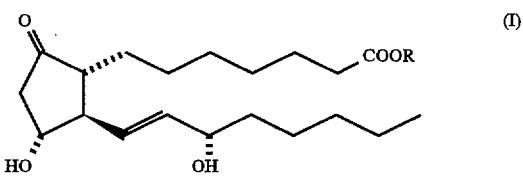

wherein R is (i) —CH$_2$CH$_2$—O—CO—R$^1$, or (ii) —CH$_2$CH$_2$—O—CO—CH$_2$—O—R$^2$, and R$^1$ and R$^2$ each independently is C10–20 alkyl; or a cyclodextrin clathrate thereof.

2. A compound according to claim 1, wherein R is (i) —CH$_2$CH$_2$—O—CO—R$^1$, and $R^1$ is C10–12 alkyl.

3. A compound according to claim 1, wherein R is (ii) —$CH_2CH_2$—O—CO—$CH_2$—O—$R^2$, and $R^2$ is C11–17 alkyl.

4. A compound according to claim 2 which is $PGE_1$ 2-(dodecanoyloxy)ethyl ester.

5. A compound according to claim 3 which is selected from the group consisting of $PGE_1$ 2-(dodecyloxyacetoxy) ethyl ester and $PGE_1$ 2-(hexadecyloxyacetoxy)ethyl ester.

6. A liposome formulation comprising:

a $PGE_1$ ester derivative of formula (I) as defined in claim 1 or a cyclodextrin clathrate thereof, as active ingredient; and a liposome membrane material.

7. A liposome formulation according to claim 6, wherein the liposome membrane material comprises dimyristoylphosphatidylcholine.

8. A liposome formulation according to claim 6, wherein the liposome membrane material comprises egg lecithin.

9. A liposome formulation according to claim 6, wherein the $PGE_1$ ester derivative is $PGE_1$ 2-(dodecanoyloxy)ethyl ester.

10. A liposome formulation according to claim 6, wherein the $PGE_1$ ester derivative is $PGE_1$ 2-(dodecyloxyacetoxy) ethyl ester or $PGE_1$ 2-(hexadecyloxyacetoxy)ethyl ester.

11. A pharmaceutical composition which comprises, as active ingredient, an effective amount of a prostaglandin $E_1$ derivative of formula (I) as defined in claim 1, or a cyclodextrin clathrate thereof.

12. A method for the prevention and treatment of peripheral circulatory disorder, decubitus, or skin ulcers, or for blood flow maintenance after reconstructive vascular surgery, which comprises administering an effective amount of a prostaglandin $E_1$ derivative of formula (I) as defined in claim 1, or a cyclodextrin clathrate thereof.

* * * * *